(12) United States Patent
Schimperna et al.

(10) Patent No.: US 8,981,118 B2
(45) Date of Patent: Mar. 17, 2015

(54) PROCESS FOR THE PREPARATION OF BENZODITHIOPHENE COMPOUNDS

(71) Applicant: Eni S.p.A., Rome (IT)

(72) Inventors: Giuliana Schimperna, Novara (IT); Gabriele Bianchi, Novara (IT)

(73) Assignee: Eni S.p.A., Rome (IT)

( * ) Notice: Subject to any disclaimer, the term of this patent is extended or adjusted under 35 U.S.C. 154(b) by 0 days.

(21) Appl. No.: 14/091,584

(22) Filed: Nov. 27, 2013

(65) Prior Publication Data

US 2014/0155631 A1    Jun. 5, 2014

(30) Foreign Application Priority Data

Nov. 30, 2012  (IT) .............................. MI2012A2052

(51) Int. Cl.
    *C07D 495/04*    (2006.01)
(52) U.S. Cl.
    CPC .................................. *C07D 495/04* (2013.01)
    USPC ............................................ 549/43; 549/29
(58) Field of Classification Search
    CPC .................................................... C07D 495/04
    USPC ..................................................... 549/29, 43
    See application file for complete search history.

(56) References Cited

U.S. PATENT DOCUMENTS 8,299,272 B2 * 10/2012 Miura et al. .................... 549/43
8,529,794 B2 *  9/2013 Heeney et al. ................ 252/500

* cited by examiner

*Primary Examiner* — Golam M Shameem
(74) *Attorney, Agent, or Firm* — Tarolli, Sundheim, Covell & Tummino LLP

(57) ABSTRACT

Process for the preparation of a benzodithiophene compound which comprises reacting at least one monohalogenated dithiophene compound with at least one internal alkyne, in the presence of at least one catalyst containing palladium and of at least one co-catalyst containing copper in oxidation state +1.

Said benzodithiophene compound, after suitable functionalization and polymerization, can be advantageously used in the construction of photovoltaic devices (or solar devices) such as, for example, photovoltaic cells (or solar cells), photovoltaic modules (or solar modules), on either rigid and flexible supports. Furthermore, said benzodithiophene compound can be advantageously used as a constituent unit of luminescent solar concentrators (LSCs). Said benzodithiophene compound can also be advantageously used as a precursor of monomeric units in the preparation of semiconductor polymers.

17 Claims, No Drawings

PROCESS FOR THE PREPARATION OF BENZODITHIOPHENE COMPOUNDS

The present invention relates to a process for the preparation of a benzodithiophene compound.

More specifically, the present invention relates to a process for the preparation of a benzodithiophene compound which comprises reacting at least one monohalogenated dithiophene compound with at least one internal alkyne, in the presence of at least one catalyst containing palladium and of at least one co-catalyst containing copper in oxidation state +1.

Said benzodithiophene compound, after suitable functionalization and polymerization, can be advantageously used in the construction of photovoltaic devices (or solar devices) such as, for example, photovoltaic cells (or solar cells), photovoltaic modules (or solar modules), on either rigid and flexible supports. Furthermore, said benzodithiophene compound can be advantageously used as a constituent unit of luminescent solar concentrators (LSCs). Said benzodithiophene compound can also be advantageously used as a precursor of monomeric units in the preparation of semiconductor polymers.

Photovoltaic devices (or solar devices) are devices capable of converting the energy of a light radiation into electric energy. At present, most photovoltaic devices (or solar devices) which can be used for practical applications exploit the physico-chemical properties of photoactive materials of the inorganic type, in particular high-purity crystalline silicon. As a result of the high production costs of silicon, however, scientific research has been orienting its efforts towards the development of alternative organic materials having a conjugated, oligomeric or polymeric structure, in order to obtain organic photovoltaic devices (or solar devices) such as, for example, organic photovoltaic cells (or solar cells). Unlike high-purity crystalline silicon, in fact, said organic materials are characterized by a relative synthesis easiness, a low production cost, a reduced weight of the relative organic photovoltaic devices (or solar devices), in addition to allowing the recycling of said organic materials at the end of the life-cycle of the organic photovoltaic device (or solar device) in which they are used.

The advantages indicated above make the use of said organic materials energetically and economically appealing in spite of any possible lesser efficiencies (η) of the organic photovoltaic devices (or solar devices) thus obtained with respect to inorganic photovoltaic devices (or solar devices).

The functioning of organic photovoltaic devices (or solar devices) such as, for example, organic photovoltaic cells (or solar cells), is based on the combined use of an electron acceptor compound and of an electron donor compound. In the state of the art, the most widely-used electron acceptor compounds in organic photovoltaic devices (or solar devices) are fullerene derivatives, in particular PC61BM (6,6-phenyl-$C_{61}$-methyl butyric ester) or PC71BM (6,6-phenyl-$C_{71}$-methyl butyric ester), which have led to the greatest efficiencies when mixed with electron donor compounds selected from π-conjugated polymers such as, for example, polythiophenes (η>5%), polycarbazoles (η>6%), derivatives of poly(thienothiophene)-benzodithiophene (PTB) (η>8%).

The elementary conversion process of light into electric current in an organic photovoltaic cell (or solar cell) takes place through the following steps:

1. absorption of a photon on the part of the electron donor compound with the formation of an exciton, i.e. a pair of "electron-electronic gap (or hole)" charge transporters;

2. diffusion of the exciton in a region of the electron donor compound as far as the interface with the electron acceptor compound;

3. dissociation of the exciton in the two charge transporters: (electron (−) in the acceptor phase (i.e. in the electron acceptor compound) and electronic gap [(or hole) (+)] in the donor phase (i.e. in the electron donor compound);

4. transporting of the charges thus formed to the cathode (electron through the electron acceptor compound) and to the anode [electronic gap (or hole), through the electron donor compound], with the generation of an electric current in the circuit of the organic photovoltaic cell (or solar cell).

The photo-absorption process with the formation of the exciton and the subsequent yielding of the electron to the electron acceptor compound leads to the excitation of an electron from the HOMO (Highest Occupied Molecular Orbital) to the LUMO (Lowest Unoccupied Molecular Orbital) of the electron donor compound and, subsequently, the passage from this to the LUMO of the electron acceptor compound.

As the efficiency of an organic photovoltaic cell (or solar cell) depends on the number of free electrons which are generated by dissociation of the excitons, which can in their turn be directly correlated to the number of photons absorbed, one of the structural characteristics of the electron donor compounds which mostly influences said efficiency is the difference in energy existing between the HOMO and LUMO orbitals of the electron donor compound, i.e. the so-called band-gap. The maximum value of the wave-length at which the electron donor compound is capable of collecting and effectively converting photons into electric energy, i.e. the so-called "light-harvesting" or "photon harvesting" process, depends, in particular, on this difference. In order to obtain acceptable electric currents, the band-gap, i.e. the difference in energy between HOMO and LUMO of the donor compound, if on one side must not be excessively high, in order to allow the absorption of the greatest number of photons, on the other side, must not be excessively low, as it could reduce the voltage at the electrodes of the device.

In the simplest way of operating, organic photovoltaic cells (or organic solar cells) are produced by introducing a thin layer (about 100 nanometers) of a mixture of the electron acceptor compound and the electron donor compound (architecture known as "bulk heterojunction"), between two electrodes, usually consisting of indium-tin oxide (ITO) (anode) and aluminium (Al) (cathode). In order to obtain a layer of this type, a solution of the two compounds is generally prepared, and a photoactive film is then created on the anode [indium-tin oxide (ITO)] starting from this solution, resorting to suitable deposition techniques such as, for example, "spin-coating", "spray-coating", "ink-jet printing", and the like. Finally, the counter-electrode [i.e. the aluminium cathode (Al)] is deposited on the dried film. Optionally, other additional layers can be introduced between the electrodes and the photoactive film, capable of exerting specific functions of an electrical, optical or mechanical nature.

Generally, in order to facilitate the electron gaps (or holes) in reaching the anode [indium-tin oxide (ITO)] and at the same time block the transfer of the electrons, thus improving the collection of the charges on the part of the electrode and inhibiting recombination phenomena, a film is deposited, before creating the photoactive film starting from the mixture of acceptor compound and of donor compound as described above, starting from an aqueous suspension of PEDOT:PSS [poly(3,4-ethylenedioxythiophene)polystyrene sulfonate], resorting to suitable deposition techniques such as, for example, "spin-coating", "spray-coating", "ink-jet printing", and the like.

The electron donor compound most commonly used in the production of organic photovoltaic cells (or organic solar cells) is regioregular poly(3-hexylthiophene) (P3HT). This polymer has optimum electronic and optical characteristics (good values of the HOMO and LUMO orbitals, a good molar absorption coefficient), a good solubility in the solvents used for producing the photovoltaic cells (or solar cells) and a reasonable mobility of the electronic gaps.

Other examples of polymers that can be advantageously used as electron donor compounds are: PCDTBT {poly[N-9"-heptadecanyl-2,7-carbazole-alt-5,5-(4',7'-di-2-thienyl-2', 1',3'-benzothia-diazole]}, the polymer PCPDTBT {poly[2,6-(4,4-bis-(2-ethylhexyl)-4H-cyclopenta[2,1-b;3,4-b']-dithiophene)-alt-4,7-(2,1,3-benzothiadiazole)]}.

Electron donor compounds containing benzodithiophene units having a structure similar to poly(3-hexylthiophene) (P3HT) are also known, wherein, however, the thiophene units are planarized by means of benzene rings. This characteristic not only increases the oxidation potential of these electron donor compounds, but also improves their stability to air and increases the molecular order during the production of the photoactive film: this produces excellent charge transfer properties [electrons or electronic gaps (holes)]. The use of electron donor compounds containing benzodithiophene units can therefore allow the production of photovoltaic devices (or solar devices) with improved performances.

Electron donor compounds containing benzodithiophene units are described, for example, by Huo L. et al. in the article: "Synthesis of a polythieno[3,4-b]thiophene derivative with a low-lying HOMO level and its application in polymer solar cells", "*Chemical Communication*" (2011), Vol. 47, pages 8850-8852. In said article, the preparation of a polythieno[3,4-b]thiophene derivative by the copolymerization of a planar benzodithiophene having a deeper HOMO with a thieno[3,4-b]thiophene unit, is described.

It is known that benzodithiophene and/or its isomers [e.g., benzo[1,2-b:4,5-b']dithiophene or (BDT) and benzo[2,1-b:3,4-b']dithiophene or (BDP)], are compounds of significant interest whose synthesis has been the object of numerous research projects.

Benzodithiophene and/or its isomers can generally be prepared by means of three different processes.

A first process comprises an annulation reaction known as McMurry reaction, of a diketone-2,2'-dithiophene. Said annulation reaction is generally carried out in the presence of catalysts containing titanium and zinc, at a temperature ranging from 60° C. to 80° C., in the presence of solvents such as, for example, tetrahydrofuran (THF), dioxane, for a time ranging from 8 hours to 12 hours. The yields to benzodithiophene and/or its isomers generally range from 30% to 90%.

Further details relating to said first process can be found, for example, in the article of Yoshida S. et al.: "Novel Electron Acceptors Bearing a Heteroquinonoid System. 4. Syntheses, Properties, and Charge-Transfer Complexes of 2,7-Bis(dicyanomethylene)-2,7-dihydrobenzo[2,1-b:3,4-b'] dithiophene, 2,7-Bis-(dicyanomethylene)-2,7-dihydrobenzo-[1,2-b:4,3-b']-dithiophene, and 2,6-Bis(dicyanomethylene)-2,6-dihydrobenzo-[1,2-b:4,5-b']-dithiophene", "*Journal of Organic Chemistry*" (1994), Vol. 59, No. 11, pages 3077-3081. In said article, the preparation of a dicyanoalkylene-benzodithiophene starting from isomers of benzodithiophene such as, for example, benzo[2,1-b:3,4-b']dithiophene, benzo[1,2-b:4,3-b']dithiophene, benzo[1,2-b:4,5-b']dithiophene, is described. Said isomers of benzodithiophene can be obtained by the reaction of a 2,2'-dithiophene-3,3'-dicarbaldehyde with titanium tetrachloride (TiCl$_4$) and metallic zinc (Zn), in the presence of anhydrous tetrahydrofuran.

Further details relating to said first process can also be found in the article of Rajca S. et al.: "Functionalized Thiophene-Based [7]Helicene: Chirooptical Properties versus Electron Delocalization", "*Journal of Organic Chemistry*" (2009), Vol. 74, No. 19, pages 7504-7513. In said article, the preparation of a functionalized [7]helicene, enantiomerically pure, deriving from a di(benzodithiophene) functionalized with four heptyl groups, is described. It also described the preparation of a benzodithiophene by the reaction of a 3,4-dibromothiophene with lithium isopropylamide (LDA) to give a dilithiate derivative which is subsequently reacted with N-methoxy-N-methyloctanamide to give the corresponding diketone. Said diketone is subsequently reacted with titanium tetrachloride (TiCl$_4$) and metallic zinc obtaining benzodithiophene.

The second process provides for an annulation reaction between a diiodo-dithiophene and an excess of internal alkyne. This reaction is generally carried out in the presence of catalysts containing palladium, at a temperature ranging from 120° C. to 140° C., in the presence of solvents such as, for example, N,N-dimethylformamide (DMF), toluene, o-xylene, for a time ranging from 4 hours to 48 hours. The yields generally range from 50% to 90%.

Further details relating to this second process can be found, for example, in the article of Watanabe H. et al.: "Synthesis of Alkylated Benzo[2,1-b:3,4-b']dithiophenes by Annulative Coupling and Their Direct Arylation under Palladium Catalysis", "*Chemistry Letters*" (2007), Vol. 36, No. 11, pages 1336-1337. In said article, the preparation of a dialkyl derivative of benzo[2,1-b:3,4-b']dithiophene by the reaction of 3,3'-diiodo-2,2'-dithiophene with 4-octyne, in the presence of N,N-dimethylformamide (DMF) and of palladium(II)acetate Pd(OAc)$_2$ and N-methyl-dicyclohexylamine as catalyst, is described.

The third process provide for an annulation reaction between a dibromo-dithiophene and a vic-bis(pinacolatoboryl)alkene or a vic-bis(pinacolatoboryl)phenanthrene. Said reaction is generally carried out in the presence of catalysts containing palladium, at a temperature ranging from 60° C. to 80° C., in the presence of solvents such as, for example, tetrahydrofuran (THF), toluene, for a time ranging from 24 hours to 48 hours. The yields generally range from 50% to 90%.

Further details relating to said third process can be found, for example, in the article of Shimizu M. et al.: "Palladium-Catalyzed Annulation of vic-Bis(pinacolatoboryl)alkenes and -phenanthrenes with 2,2'-Dibromobiaryls: Facile Synthesis of Functionalized Phenatrenes and Dibenzo[g,p]-chrysenes", "*Angewandte Chemie International Edition*" (2008), Vol. 47, pages 8096-8099. In said article, the preparation of a dialkyl-benzodithiophene by the reaction of a dibromo-dithiophene with a vic-bis(pinacolatoboryl)alkene in tetrahydrofuran (THF), in the presence of potassium carbonate (K$_2$CO$_3$) and of tetrakis(triphenylphosphine)-palladium(0) [Pd(PPh$_3$)$_4$] as catalyst, is described.

Although the above processes, however, allow benzodithiophene and/or its isomers to be obtained with good yields, generally higher than or equal to 50%, they can have various drawbacks. In particular:

there are numerous synthetic steps for obtaining the desired end-compound;
    corrosive and/or flammable reagents are frequently used, such as, for example, titanium tetrachloride, lithium diisopropylamide (LDA), with consequent problems relating to safety, for both the environment and the operators, with consequent higher costs of production and of disposal of the waste-products;

dihalogenated starting compounds are often used, such as, for example, diiodo-dithiophene or dibromo-dithiophene, which are generally costly and have a poor stability.

Processes for the preparation of polycyclic aromatic compounds through annulation reactions of aryl halides with internal alkynes, in the presence of palladium compounds as catalysts, are also known in the art.

Larock R. C. et al., in the article: "Synthesis of Polycyclic Aromatic Hydrocarbons by the Pd-Catalyzed Annulation of Alkynes", "*Journal of Organic Chemistry*" (1997), Vol. 62, No. 22, pages 7536-7537, for example, describe an annulation reaction with internal alkynes according to the following Scheme 1:

Scheme 1

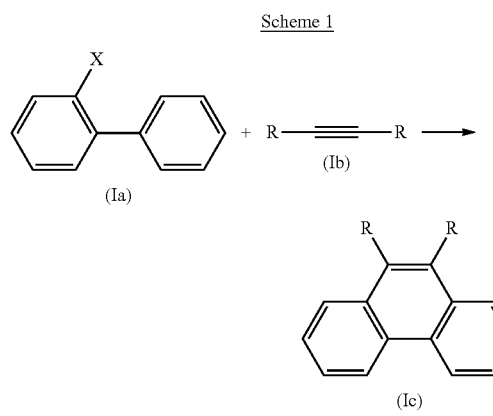

wherein an aryl halide having formula (Ia) such as, for example, 2-iodo-biphenyl, is reacted with an internal alkyne having formula (Ib) such as, for example, diphenylacetylene, in the presence of a catalyst containing palladium such as, for example, palladium(II)acetate ([Pd(OAc)$_2$]), a solvent such as, for example, dimethylformamide (DMF), and a base such as, for example, sodium acetate (NaOAc), obtaining a disubstituted phenanthrene having formula (Ic).

Huang H. et al., in the article "Palladium-catalyzed three-component domino reaction for the preparation of benzo[b]thiophene and related compounds", "*Organic and Biomolecular Chemistry*" (2011), Vol. 9, pages 5036-5038, describe a three-component domino annulation reaction, according to the following Scheme 2:

Scheme 2

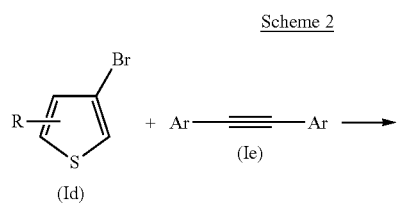

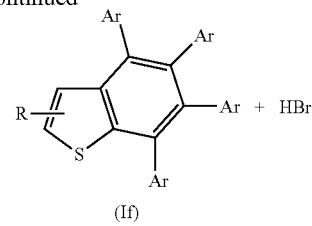

wherein a bromothiophene having formula (Id) such as, for example, 3-bromothiophene, is reacted with an internal alkyne having formula (Ie) such as, for example, diphenylacetylene, in the presence of a catalyst containing palladium such as, for example, palladium(II)acetate ([Pd(OAc)$_2$]), a phosphine such as, for example, tricyclohexylphosphine [P(Cy)$_3$], a solvent such as, for example, dimethylformamide (DMF), and a base such as, for example, sodium carbonate (Na$_2$CO$_3$), obtaining a tetra-aryl-benzoalkyl-thiophene having formula (If).

Gericke K. M. et al., in the article: "The versatile role of norbornene in C—H functionalization processes: concise synthesis of tetracyclic fused pyrroles via a threefold domino reaction", "*Tetrahedron*" (2008), Vol. 64, pages 6002-6014 describe an annulation reaction according to Scheme 3:

Scheme 3

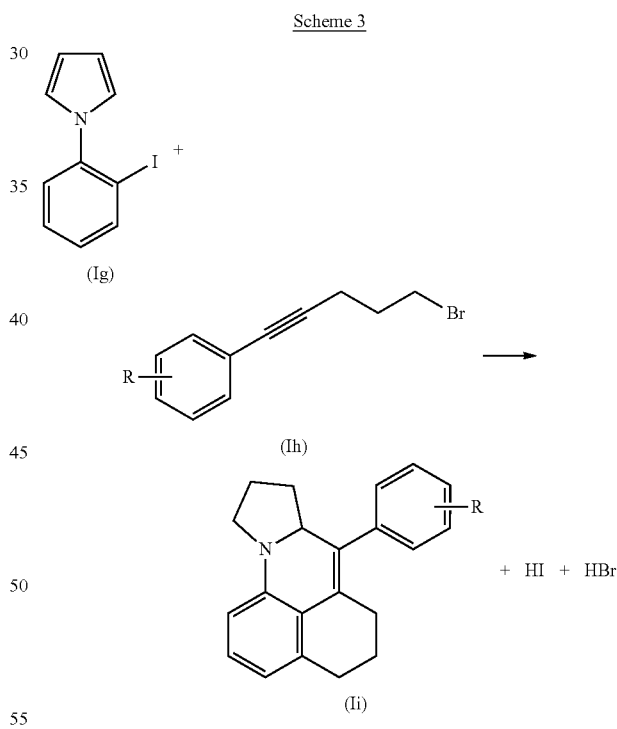

wherein an aryl iodide such as, for example, 1,2-iodophenyl-1-H-pyrrole having formula (Ig), is reacted with an internal bromo-alkylarylalkyne having formula (Ih) such as, for example, (5-bromo-1-pentenyl)benzene, in the presence of a catalyst containing palladium, such as, for example, palladium(II)chloride (PdCl$_2$) associated with triphenylphosphine (PPh$_3$) as ligand, in the presence of a solvent such as, for example, acetonitrile (CH$_3$CN), and of a base such as, for example, caesium carbonate (Cs$_2$CO$_3$), obtaining a 7-phenyl-5,6-dihydro-4H-benzo[d,e]pyrrole[1,2-α]-quinoline having formula (Ii).

Italian patent application MI2011A002303 in the name of the Applicant, describes a process for the preparation of a benzodithiophene compound which comprises reacting at least one monohalogenated dithiophene compound with at least one internal alkyne.

Although the above process allows benzodithiophene compounds to be obtained with good yields (i.e. yields ranging from 70% to 80%), it requires lengthy reaction times (preferably times ranging from 15 hours to 72 hours) with a consequent increase in the process costs. Furthermore, lengthy reaction times can cause the degradation of the benzodithiophene compounds obtained.

The Applicant has therefore considered the problem of finding a process for the preparation of a benzodithiophene compound which is capable of overcoming the drawbacks indicated above.

The Applicant has now found that the preparation of a benzodithiophene compound can be advantageously carried out by means of a process which comprises reacting at least one monohalogenated dithiophene compound with at least one internal alkyne, in the presence of at least one catalyst containing palladium and of at least one co-catalyst containing copper in oxidation state +1.

Numerous advantages can be obtained by operating according to the above process, such as, for example:
  reduction in the number of synthetic steps with a relative reduction in the processing times and process costs;
  use of monohalogenated starting products which are generally more economical and more stable than the corresponding dihalogenated compounds;
  use of internal alkynes which are more economical and more stable than diboron esters of internal alkenes;
  greater safety conditions [e.g., absence of corrosive and/or flammable reagents such as, for example, titanium tetrachloride, lithium diisopropylamide (LDA)] for both the health of the operators and also from an environmental point of view;
  relatively low temperatures and, in particular, short reaction times thus avoiding the possible degradation of the product obtained, and higher process costs.

Furthermore, the above process allows a benzodithiophene compound to be obtained with high yields (i.e. yields ≥85%).

An object of the present invention therefore relates to a process for the preparation of a benzodithiophene compound having general formula (I):

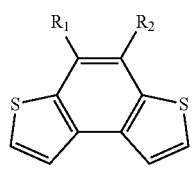

(I)

wherein:
  $R_1$ and $R_2$, each independently, represent a hydrogen atom, a linear or branched $C_1$-$C_{20}$, preferably $C_1$-$C_{12}$, alkyl group, a cycloalkyl group optionally substituted, an aryl group optionally substituted, a heteroaryl group optionally substituted;
said process comprising reacting at least one monohalogenated dithiophene compound having general formula (II):

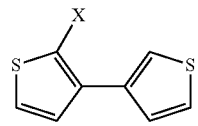

(II)

wherein X represents a halogen atom selected from iodine, chlorine, bromine, preferably iodine; with at least one internal alkyne having general formula (III):

(III)

wherein $R_1$ and $R_2$ have the same meanings defined above; in the presence of at least one catalyst containing palladium and of at least one co-catalyst containing copper in oxidation state +1 having general formula (IV):

$$CuX_1 \qquad (IV)$$

wherein $X_1$ represents a halogen atom selected from iodine, chlorine, bromine, preferably iodine.

For the aim of the present description and of the following claims, the definitions of the numerical ranges always include the extremes, unless otherwise specified.

The term "$C_1$-$C_{20}$ alkyl group" refers to a linear or branched alkyl group having from 1 to 20 carbon atoms. Specific examples of $C_1$-$C_{20}$ alkyl group are: methyl, ethyl, n-propyl, iso-propyl, n-butyl, iso-butyl, t-butyl, pentyl, ethylhexyl, hexyl, heptyl, octyl, nonyl, decyl, dodecyl.

The term "cycloalkyl group" refers to a cycloalkyl group having from 3 to 10 carbon atoms. Said cycloalkyl group can be optionally substituted with one or more groups, equal to or different from each other, selected from: halogen atoms such as, for example, fluorine, chlorine, preferably fluorine, hydroxyl groups, $C_1$-$C_{20}$ alkyl groups, $C_1$-$C_{20}$ alkoxyl groups, cyano groups, amino groups, nitro groups. Specific examples of cycloalkyl group are: cyclopropyl, 2,2-difluorocyclopropyl, cyclobutyl, cyclopentyl, cyclohexyl, methylcyclohexyl, methoxycyclohexyl, fluorocyclohexyl, phenylcyclohexyl.

The term "aryl group" refers to an aromatic carbocyclic group. Said aromatic carbocyclic group can be optionally substituted with one or more groups, equal to or different from each other, selected from: halogen atoms such as, for example, fluorine, chlorine, preferably fluorine, hydroxyl groups, $C_1$-$C_{20}$ alkyl groups, $C_1$-$C_{20}$ alkoxyl groups, cyano groups, amino groups, nitro groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, nitrophenyl, dimethylaminophenyl, naphthyl, phenylnaphthyl, phenanthrene, anthracene.

The term "heteroaryl group" refers to an aromatic, penta- or hexa-atomic heterocyclic group, also benzocondensed or heterobicyclic, containing from 1 to 4 heteroatoms selected from nitrogen, oxygen, sulfur, silicon, selenium, phosphorous. Said heteroaryl group can be optionally substituted with one or more groups, equal to or different from each other, selected from: halogen atoms, such as, for example, fluorine, chlorine, preferably fluorine, hydroxyl groups, $C_1$-$C_{20}$ alkyl groups, $C_1$-$C_{20}$ alkoxyl groups, cyano groups, amino groups, nitro groups. Specific examples of heteroaryl groups are: pyridine, methylpyridine, methoxypyridine, phenylpyridine, fluoropyridine, pyrimidine, pyridazine, pyrazine, triazine, tetrazine, quinoline, quinoxaline, quinazoline, furan, thiophene, hexylthiophene, pyrrole, oxazole, thiazole, isooxazole, isothiazole, oxadiazole, thiadiazole, pyrazole, imidazole, triazole, tetrazole, indole, benzofuran, benzothiophene, benzooxazole, benzothiazole, benzooxadiazole, benzothiadiazole, benzopyrazole, benzimidazole, benzotriazole, triazolopyridine, triazolpyrimidine, coumarine.

The above process can be carried out according to the following Scheme 4:

Scheme 4

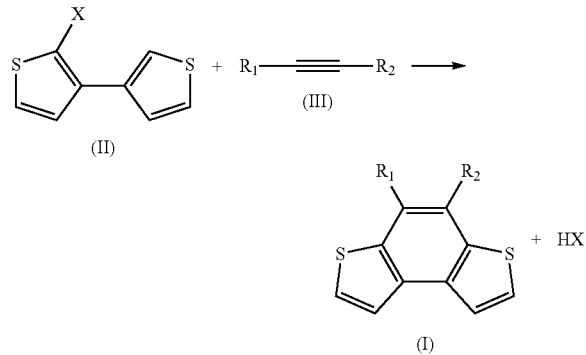

wherein X, $R_1$ and $R_2$, have the same meanings described above.

According to a preferred embodiment of the present invention, said monohalogenated dithiophene compound having general formula (II) ad said internal alkyne having general formula (III) can be used in a molar ratio ranging from 1:2 to 1:10, preferably ranging from 1:2 to 1:5.

According to a preferred embodiment of the present invention, said catalyst containing palladium can be selected from: palladium compounds in oxidation state 0 or +2 such as, for example, palladium(II)chloride [$PdCl_2$], palladium(II)acetate [$Pd(OAc)_2$], bis(dibenzylidene)palladium(0) [$Pd_2(dba)_3$ wherein dba=$C_6H_5CH$=$CHCOCH$=$CHC_6H_5$], bis(acetonitrile)palladium(II)-chloride [$Pd(CH_3CN)_2Cl_2$], bis(triphenylphosphine)-palladium(II)chloride [$Pd(PPh_3)_2Cl_2$], bis(triphenyl-phosphine)palladium(II)acetate [$Pd(PPh_3)_2(OAc)_2$], tetrakis(triphenylphosphine)palladium(0) [$Pd(PPh_3)_4$], or mixtures thereof. Said catalyst containing palladium is preferably selected from palladium(II)acetate [$Pd(OAc)_2$], bis(triphenylphosphine)palladium(II)-chloride [$Pd(PPh_3)_2Cl_2$].

According to a preferred embodiment of the present invention, said monohalogenated dithiophene compound having general formula (II) and said catalyst containing palladium can be used in a molar ratio ranging from 100:0.1 to 100:8, preferably ranging from 100:0.4 to 100:6.

According to a preferred embodiment of the present invention, said monohalogenated dithiophene compound having general formula (II) and said catalyst containing copper in oxidation state +1 having general formula (IV) can be used in a molar ratio ranging from 1:0.2 to 1:1, preferably ranging from 1:0.3 to 1:0.6.

According to a further preferred embodiment of the present invention, said process relates to the preparation of 6,5-dibutylbenzo[1,2-b:4,3-b']dithiophene corresponding to a benzodithiophene compound having general formula (I), wherein $R_1$ and $R_2$ represent a n-butyl group, said process comprising reacting 2-iodo-3,3'-dithiophene corresponding to a monohalogenated dithiophene compound having general formula (II), wherein X represents an iodine atom, with 5-decyne corresponding to an internal alkyne having general formula (III), wherein $R_1$ and $R_2$ represent a n-butyl group.

According to a preferred embodiment of the present invention, said process can be carried out in the presence of at least one weak organic base.

According to a preferred embodiment of the present invention, said weak organic base can be selected, for example, from: carboxylates of alkaline metals (e.g., sodium, potassium, caesium) or of alkaline earth metals (e.g., magnesium, calcium) such as, for example, potassium acetate, sodium acetate, caesium acetate, magnesium acetate, calcium acetate, potassium propionate, sodium propionate, caesium propionate, magnesium propionate, calcium propionate, or mixtures thereof; carbonates of alkaline metals (e.g., lithium, sodium, potassium, caesium) or of alkaline earth metals (e.g., magnesium, calcium) such as, for example, lithium carbonate, potassium carbonate, sodium carbonate, caesium carbonate, magnesium carbonate, calcium carbonate, or mixtures thereof; bicarbonates of alkaline metals (e.g., lithium, sodium, potassium, caesium) or of alkaline earth metals (e.g., magnesium, calcium) such as, for example, lithium bicarbonate, potassium bicarbonate, sodium bicarbonate, caesium bicarbonate, magnesium bicarbonate, calcium bicarbonate, or mixtures thereof; or mixtures thereof. Said weak organic base is preferably selected from potassium acetate, potassium carbonate.

According to a preferred embodiment of the present invention, said monohalogenated dithiophene compound having general formula (II) and said weak organic base can be used in a molar ratio ranging from 1:2.2 to 1:20, preferably ranging from 1:2.5 to 1:4.

According to a preferred embodiment of the present invention, said monohalogenated dithiophene compound having general formula (II) can be used at a molar concentration ranging from 0.05 mmoles to 2 mmoles, preferably ranging from 0.1 mmoles to 1.5 mmoles.

According to a preferred embodiment of the present invention, said process can be carried out in the presence of at least one dipolar aprotic organic solvent.

According to a preferred embodiment of the present invention, said dipolar aprotic organic solvent can be selected, for example, from: N,N-dimethylacetamide (DMAc), dimethylsulfoxide (DMSO), N-methylpyrrolidone (NMP), N,N-dimethylformamide (DMF), or mixtures thereof. Said dipolar aprotic organic solvent is preferably selected from N,N-dimethylacetamide (DMAc), N,N-dimethylformamide (DMF).

According to a preferred embodiment of the present invention, said monohalogenated dithiophene compound having general formula (II) can be used in said dipolar aprotic organic solvent in such a quantity as to have a molar concentration in said solvent ranging from 0.05 M to 0.5 M, preferably ranging from 0.08 M to 0.2 M.

According to a preferred embodiment of the present invention, said process can be carried out in the presence of at least one weak organic acid.

According to a preferred embodiment of the present invention, said weak organic acid can be selected, for example, from: acetic acid, propionic acid, pivalic acid, or mixtures thereof. Said weak organic acid is preferably pivalic acid.

According to a preferred embodiment of the present invention, said monohalogenated dithiophene compound having general formula (II) and said weak organic acid can be used in a molar ratio ranging from 1:0.1 to 1:1, preferably ranging from 1:0.2 to 1:0.5.

According to a preferred embodiment of the present invention, said process can be carried out at a temperature ranging from 80° C. to 130° C., preferably ranging from 100° C. to 120° C.

According to a preferred embodiment of the present invention, said process can be carried out for a time ranging from 30 minutes to 2 hours, preferably ranging from 45 minutes to 1.5 hours.

The monohalogenated dithiophene compound having general formula (II) can be obtained according to processes known in the art, for example, by halogenations of the corresponding dithiophene compounds or through coupling reactions catalyzed by copper compounds. Further details relating to these processes can be found, for example, in the article of Huang W. et al.: "An Effective Strategy to Tune Supramolecular Interaction via a Spiro-Bridged Spacer in Oligothiophene-S,S-dioxides and Their Anomalous Photoluminescent Behaviour", "*Organic Letters*" (2007), Vol. 9, pages 1619-1622.

The internal alkyne having general formula (III) can be prepared according to processes known in the art, for example, by nucleophilic substitution of an alkyl acetylide on an alkyl halide as described, for example, in the article of Kirkham J. E. D. et al.: "Asymmetric synthesis of cytotoxic sponge metabolites R-strongylodiols A and B", "*Tetrahedron Letters*" (2004), Vol. 45, No. 29, pages 5645-5648; or it can be available on the market.

Some illustrative and non-limiting examples are provided for a better understanding of the present invention and for its practical embodiment.

EXAMPLE 1

Preparation of 6,5-dibutylbenzo[2,1-b:3,4-b']-dithiophene Having Formula (a)

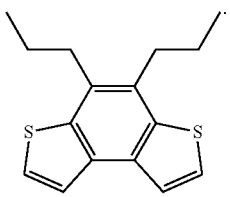

(a)

The following products were charged in order into a 100 ml Pyrex glass flask, equipped with a cooler: 1,244 mg of potassium carbonate (9 mmoles), 92 mg of pivalic acid (0.90 mmoles), 105 mg of bis(triphenylphosphine)palladium(II) chloride [Pd(PPh$_3$)$_2$Cl$_2$] (0.15 mmoles), 28 mg of copper(I) iodide (CuI) (0.15 mmoles), 376 mg of 2-iodo-3,3'-dithiophene (3 mmoles) dissolved in 5 ml of N,N-dimethylacetamide and finally 1,244 mg of 5-decyne (9 mmoles). The flask was then placed in an oil bath preheated to 100° C., for 1 hour. After cooling to room temperature (25° C.), a saturated aqueous solution of sodium chloride (50 ml) was added to the reaction mixture and the whole mixture was extracted with diethyl ether (3×25 ml). The organic phase obtained was washed to neutrality with water (3×25 ml) and subsequently anhydrified on sodium sulfate and evaporated. The residue obtained was purified by elution on a silica gel chromatographic column (eluent: heptane), obtaining 780 mg of 6,5-dibutylbenzo[2,1-b:3,4-b']dithiophene as a white solid (yield 86%).

The invention claimed is:

1. A process for the preparation of a benzodithiophene compound having general formula (I):

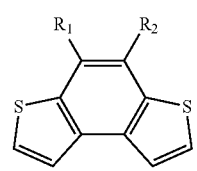

(I)

wherein:
R$_1$ and R$_2$, each independently represent a hydrogen atom, a linear or branched C$_1$—O$_{20}$ alkyl group, a cycloalkyl group optionally substituted, an aryl group optionally substituted, a heteroaryl group optionally substituted;
said process comprising reacting at least one monohalogenated dithiophene compound having general formula (II):

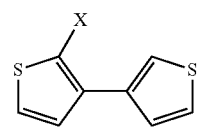

(II)

wherein X represents a halogen atom selected from iodine, chlorine, bromine; with at least one internal alkyne having general formula (III):

(III)

wherein R$_1$ and R$_2$ have the same meanings defined above;
in the presence of at least one catalyst containing palladium and of at least one co-catalyst containing copper in oxidation state +1 having general formula (IV):

CuX$_1$    (IV)

wherein X$_1$ represents a halogen atom selected from iodine, chlorine, bromine.

2. The process according to claim 1, wherein said monohalogenated dithiophene compound having general formula (II) and said internal alkyne having general formula (III) are used in a molar ratio ranging from 1:2 to 1:10.

3. The process according to claim 1, wherein said catalyst containing palladium is selected from: palladium compounds in oxidation state 0 or +2 such as palladium(II)chloride [PdCl$_2$], palladium(II)acetate [Pd(OAc)$_2$], bis(dibenzylidene)palladium(0) [Pd$_2$(dba)$_3$ wherein dba =C$_6$H$_5$CH=CHCOCH=CHC$_6$H$_5$], bis(acetonitrile)-palladium(II)chloride [Pd(CH$_3$CN)$_2$Cl$_2$], bis(triphenyl-phosphine)palladium(II)chloride [Pd(PPh$_3$)$_2$Cl$_2$], bis-(triphenylphosphine)palladium(II)acetate [Pd(PPh$_3$)$_2$(OAc)$_2$], tetrakis(triphenylphosphine)-palladium(0) [Pd(PPh$_3$)$_4$], or mixtures thereof.

4. The process according to claim 1, wherein said monohalogenated dithiophene compound having general formula (II) and said catalyst containing palladium are used in a molar ratio ranging from 100:0.1 to 100:8.

5. The process according to claim 1, wherein said monohalogenated dithiophene compound having general formula (II) and said catalyst containing copper in oxidation state +1 having general formula (IV) are used in a molar ratio ranging from 1:0.2 to 1:1.

6. The process according to claim 1, wherein said process relates to the preparation of 6,5-dibutylbenzo[2,1-b:3,4-b'] dithiophene corresponding to a benzodithiophene compound having general formula (I), wherein $R_1$ and $R_2$ represent a n-butyl group, said process comprising reacting 2-iodo-3,3'-dithiophene corresponding to a monohalogenated dithiophene compound having general formula (II), wherein X represents an iodine atom, with 5-decyne corresponding to an internal alkyne having general formula (III), wherein $R_1$ and $R_2$ represent a n-butyl group.

7. The process according to claim 1, wherein said process is carried out in the presence of at least one weak organic base.

8. The process according to claim 7, wherein said weak organic base is selected from: carboxylates of alkaline or of alkaline earth metals such as potassium acetate, sodium acetate, caesium acetate, magnesium acetate, calcium acetate, potassium propionate, sodium propionate, caesium propionate, magnesium propionate, calcium propionate, or mixtures thereof; carbonates of alkaline or of alkaline earth metals such as lithium carbonate, potassium carbonate, sodium carbonate, caesium carbonate, magnesium carbonate, calcium carbonate, or mixtures thereof; bicarbonates of alkaline or of alkaline earth metals such as lithium bicarbonate, potassium bicarbonate, sodium bicarbonate, caesium bicarbonate, magnesium bicarbonate, calcium bicarbonate, or mixtures thereof; or mixtures thereof.

9. The process according to claim 1, wherein said monohalogenated dithiophene compound having general formula (II) and said weak organic base are used in a molar ratio ranging from 1:2.2 to 1:20.

10. The process according to claim 1, wherein said process is carried out in the presence of at least one dipolar aprotic organic solvent.

11. The process according to claim 10, wherein said dipolar aprotic organic solvent is selected from: N,N-dimethylacetamide (DMAc), dimethylsulfoxide (DMSO), N-methylpyrrolidone (NMP), N,N-dimethylformamide (DMF), or mixtures thereof.

12. The process according to claim 1, wherein said monohalogenated dithiophene compound having general formula (II) is used in said dipolar aprotic organic solvent in such a quantity as to have a molar concentration in said solvent ranging from 0.05 M to 0.5 M.

13. The process according to claim 1, wherein said process is carried out in the presence of at least one weak organic acid.

14. The process according to claim 13, wherein said weak organic acid is selected from: acetic acid, propionic acid, pivalic acid, or mixtures thereof.

15. The process according to claim 1, wherein said monohalogenated dithiophene compound having general formula (II) and said weak organic acid are used in a molar ratio ranging from 1:0.1 to 1:1.

16. The process according to claim 1, wherein said process is carried out at a temperature ranging from 80° C. to 130° C.

17. The process according to claim 1, wherein said process is carried out for a time ranging from 30 minutes to 2 hours.

* * * * *